(12) United States Patent
Ruymen

(10) Patent No.: US 6,473,168 B1
(45) Date of Patent: Oct. 29, 2002

(54) METHOD AND APPARATUS FOR DETECTING IRREGULARITIES IN A PRODUCT

(76) Inventor: Marc Ruymen, Bierbeekstraat 103, B-3360 Korbeek-Lo (BE)

( * ) Notice: Subject to any disclaimer, the term of this patent is extended or adjusted under 35 U.S.C. 154(b) by 0 days.

(21) Appl. No.: 09/402,055

(22) PCT Filed: Mar. 25, 1998

(86) PCT No.: PCT/BE98/00042

§ 371 (c)(1),
(2), (4) Date: Jan. 6, 2000

(87) PCT Pub. No.: WO98/44335

PCT Pub. Date: Oct. 8, 1998

(30) Foreign Application Priority Data

Mar. 28, 1997 (BE) .............................................. 9700293

(51) Int. Cl.[7] .............................................. G01N 21/84
(52) U.S. Cl. .................................. 356/237.2; 356/237.2
(58) Field of Search .............................. 356/431, 237.2, 356/237.1, 238.3, 239.7, 429, 430; 250/559.42, 559.48, 234–236, 571, 572, 563, 574

(56) References Cited

U.S. PATENT DOCUMENTS

| | | |
|---|---|---|
| 2,672,799 A | 3/1954 | Terwilliger |
| 3,728,481 A | 4/1973 | Freohlich et al. |
| 4,072,413 A | 2/1978 | Amess |
| 5,321,495 A * | 6/1994 | Hagiwara et al. ........... 356/237 |
| 5,436,728 A * | 7/1995 | Watanabe .................... 356/431 |
| 5,448,350 A * | 9/1995 | Kohno ........................ 356/237 |

FOREIGN PATENT DOCUMENTS

EP 0345949 12/1989

OTHER PUBLICATIONS

Patent Abstract of Japan, Pub. no. 55129733, (1980).

* cited by examiner

Primary Examiner—Frank G. Font
Assistant Examiner—Layla Lauchman
(74) Attorney, Agent, or Firm—Browdy and Neimark, P.L.L.C.

(57) ABSTRACT

The invention concerns a method and a device for detecting irregularities in a product, in which at least one light band (2) is directed towards this product (7), which moves in a particular direction through a detection zone, so that said light band (2) is scattered and/or reflected by said product, and the scattered light is detected by at least one detector (12, 13) in order to detect irregularities in the product and the light stream scattered by a part of the product and captured by said detector (12, 13) is adjusted so that it is independent of the position of said part in said detection zone.

13 Claims, 7 Drawing Sheets

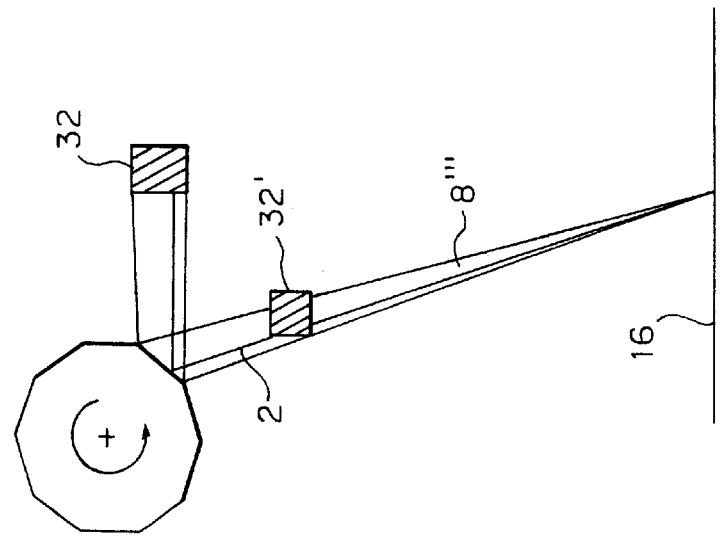
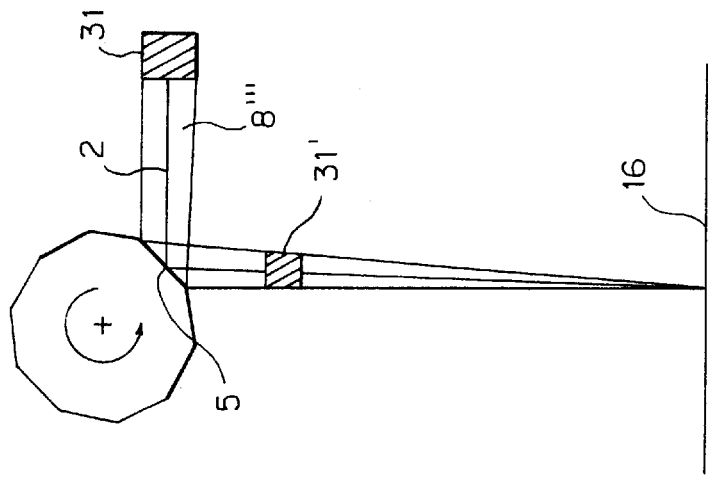
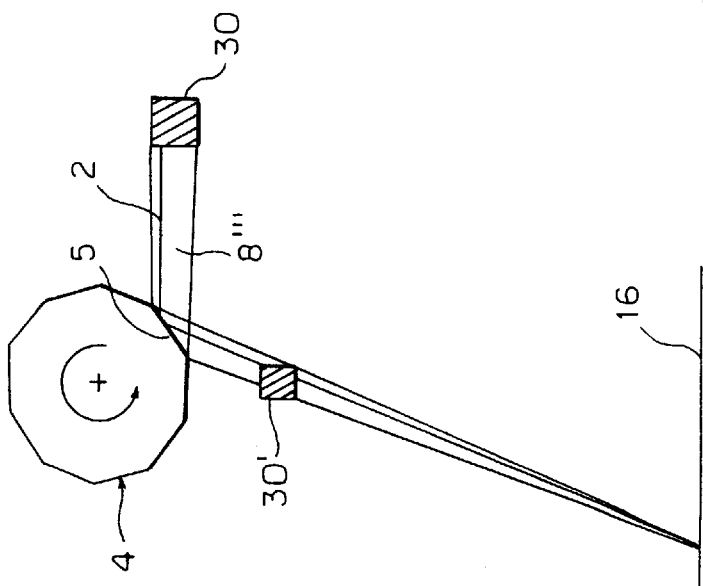

METHOD AND APPARATUS FOR DETECTING IRREGULARITIES IN A PRODUCT

CROSS REFERENCE TO RELATED APPLICATION

The present application is the national stage under 35 U.S.C. 371 of PCT/BE98/00042, filed Mar. 25, 1998.

The invention concerns a method for detecting irregularities in a product, in which at least one light band, more specifically consisting of one or more laser beams, is directed towards this product, which moves in a particular direction through a detection zone, so that said light band, which preferably moves transversely across the path of the product, is at least partially scattered and/or reflected by said product, and the scattered light is at least partially detected by at least one detector, the light stream of the scattered light then being compared with the light stream of the scattered light from a good part of the product that shows no irregularities in order to detect irregularities in the product.

By "scattered light" is meant in this description on the one hand the light which is diffusely reflected at the surface of a product, and on the other hand the light that is emitted by the product as a result of said light band at least partly penetrating it, spreading into it, and thereby making the corresponding part of the product light up.

According to the state of the art, the light stream of scattered light which is thus detected by at least one detector, is dependent on the position of said band. This means that the value of the signal generated by means of the detector, which determines whether a part of the product must be characterised as a good part or as a foreign component or a part of lower-value, is dependent on the position of the light band.

In order to avoid such dependency, the signal coming from said detector is electronically modified, for example by multiplying it by a factor which is dependent on the position of the light band, so that a signal is obtained which does not depend on the position of the light band.

These modifications require a relatively complex electronic system that considerably increases the cost price of such a method. Moreover, where a product consists of parts that are loose from one another, such corrections generally do not provide any uniform accuracy depending on the position of the light band, for the purposes of detecting irregularities in the product and characterising the latter.

The aim of the invention is to deal with this by proposing a method which does not have these disadvantages, and which ensures that irregularities in a product are detected with uniform sensitivity, and which makes it possible to carry out very good detection or classification, both qualitative and quantitative, in a very economical manner.

To this end, the light stream falling on said detector from the light scattered by part of the product is adjusted in such a manner that it is independent of the position of said part in said detection zone.

The invention also concerns a device for detecting irregularities in a product moving in a particular direction through a detection zone, with at least one detector and means to generate at least one light band directed towards said product and preferably moving perpendicular to the direction of travel of said product, in such a manner that the light from said light band is scattered and/or reflected by part of said product, where said detector is arranged so that this scattered light at least partly falls on it.

This device is characterised by the fact that between said detector and the place where the product moves through the detection zone, an adjusting element is placed that lets through only some of the light scattered by a part the product, in such a manner that the light stream of the scattered light falling on said detector is independent of the position of said part.

Said adjusting element can advantageously comprise a diaphragm with at least one calibrated opening.

In a particular embodiment of the device according to the invention, said diagram has means to adjust the size of said opening.

Said diaphragm can advantageously be provided with small, movable plates at the edge of said opening, where said plates enable the size and/or shape of the opening to be adjusted, in such a manner that the light stream falling on said detector is independent of the position of said light band.

The invention further concerns a sorting apparatus for separating foreign components or lower-value parts from good parts of a product which consists of parts that are loose from each other, where said sorting apparatus is provided with said device. For example, when the product consists of peas, the sorting apparatus makes it possible for lower-value peas such as overripe peas, and foreign objects such as small stones, stalks and suchlike, to be separated from peas that are suitable for human consumption.

Other features and advantages of the invention will be apparent from the following description of several particular embodiments of the method, the device and the sorting apparatus according to the invention; this description is given by way of example only and in no way limits the scope of the protection claimed; the reference numbers below refer to the attached drawings.

FIGS. 4, 5 and 6 are schematic representations of light bands reflected from a moving mirror.

In the different figures, the same reference figures refer to the same or similar parts.

The invention concerns among other things sorting apparatuses for products consisting of loose parts of a very different nature, such as peas, raisins, shrimps, dried or deep-frozen foods, all types of ore, drugs in tablet or capsule form, etc.

Figure 1:
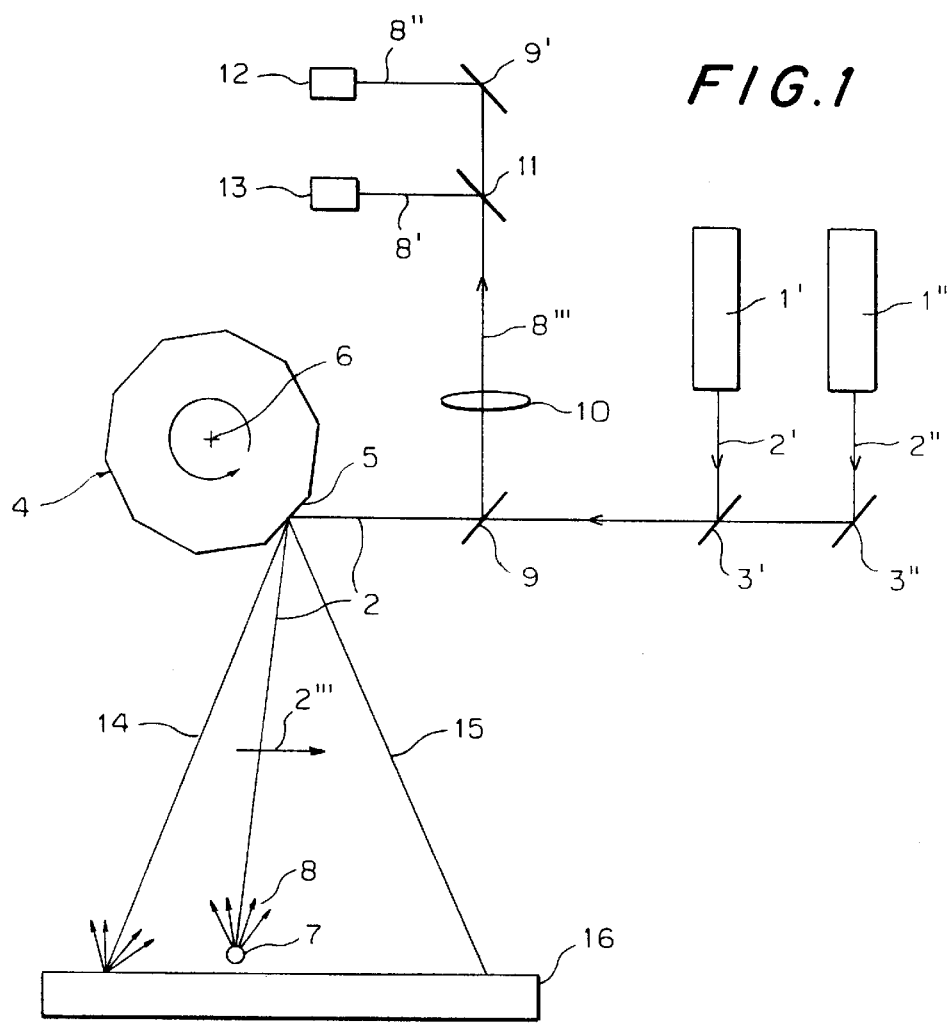
FIG. 1 is a schematic drawing showing the principle of a detection system for a sorting apparatus.

FIG. 1 shows a classic embodiment of a device which can be mounted in a sorting apparatus. This sorting apparatus is mainly used for separating lower-value parts and foreign objects from the good parts of a product. In such a sorting apparatus, a product consisting of loose parts is moved in a wide stream through the detection zone of said device, in order to enable the loose parts of the product to be characterised, and thus to distinguish between the good parts, which have essentially no irregularities, and the lower-value parts or foreign objects.

The device is provided with two light sources 1' and 1" which each generate an intense, focused band of light, respectively 2' and 2". Both light sources 1' and 1" generate light of different frequency and are brought together into a band 2 of laser beams by a selectively semi-reflecting mirror 3' (dichroic mirror) and an ordinary mirror 3". This light band 2 is reflected towards a moving, prismatic mirror 4. The faces 5 of this mirror 4 are reflective and are set at essentially the same angle to one another. Furthermore, this prismatic mirror 4 rotates around its central axis 6 at an essentially constant speed. The light band 2 falling on such a face 5 is directed towards the product to be sorted.

As a result of the rotation of the mirror 4, the light band 2 falling on the faces 5 moves transversely across the stream of parts 7 of the product. In doing so, said band 2 moves each time in the same direction between two positions 14 and 15 over the width of the stream of parts 7, as shown by the arrow 2'''. The frequency of this movement depends among other things on the speed of rotation of the mirror 4, and consists preferably of between 500 and 8,000 movements per second.

Said detection zone extends between the two positions 14 and 15 of the light band 2, where still a measurement of the scattered light is carried out.

When the light band 2, via one of the faces 5, falls on a part 7 of the product, it is scattered and/or reflected by said part 7. As shown by arrows 8, scattered light is at least partly captured by the same face 5, and, via said face 5, is led along approximately the same path as the light band 2 to a beam splitter 9 which reflects the scattered light 8''' at an angle via a lens system 10 to a so-called beam splitter 11. The beam splitter 9 has for example a central opening which enables the light band 2 from the light sources 1' and 1" to pass through unimpeded.

Possibly, scattered light may be reflected back to said detector via a face 5 of the mirror 4 that is different from the face 5 on which the light band falls.

The beam splitter 11 separates the light 8''' scattered by the product and originating from the respective light sources 1' and 1" into two light bands 8' and 8" of different frequency. Band 8' then falls on a detector 13, while band 8" falls on a detector 12 via a mirror 9'.

In the proposed embodiment of the device shown in FIG. 1, the device is provided with a background in the form of a tube 16 extending perpendicularly to the direction of displacement of said product, in such a manner that the light band 2 falls on it, where the parts 7 of the product move over said tube 16 between the latter and said mirror 4. This tube 16 preferably has the same characteristics as a good part 7 as regards the scattering of the light band 2.

Figure 2:
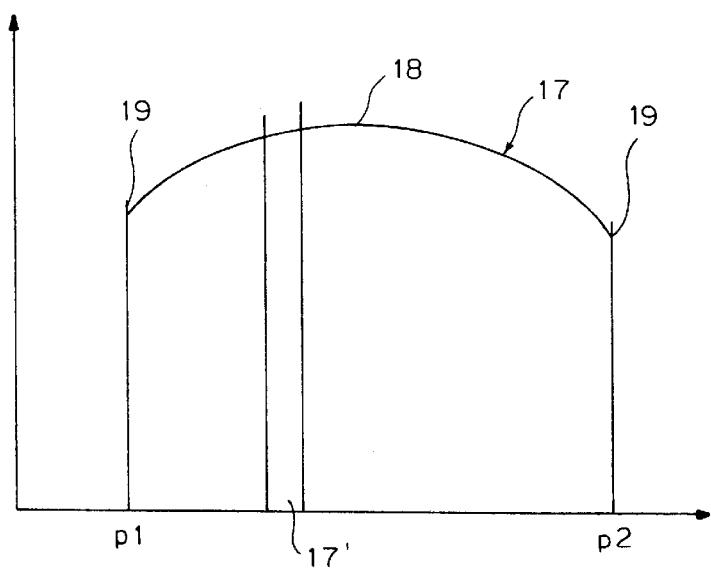
FIG. 2 is a graph of the signal supplied by a detector of a sorting apparatus.

When the light band 2 moves over said tube 16, a signal 17 is generated by the detectors 12 and 13 on which at least a part 8''' of the light scattered by said tube falls, as shown in FIG. 2. This signal is a measure of the scattered light. The Y axis shows the magnitude of this signal as a function of the position of the light band 2, shown on the X axis. When a light band 2 moves from position 14 to position 15, this corresponds to the distance between $p_1$ and $p_2$ in FIG. 2.

Figure 3:
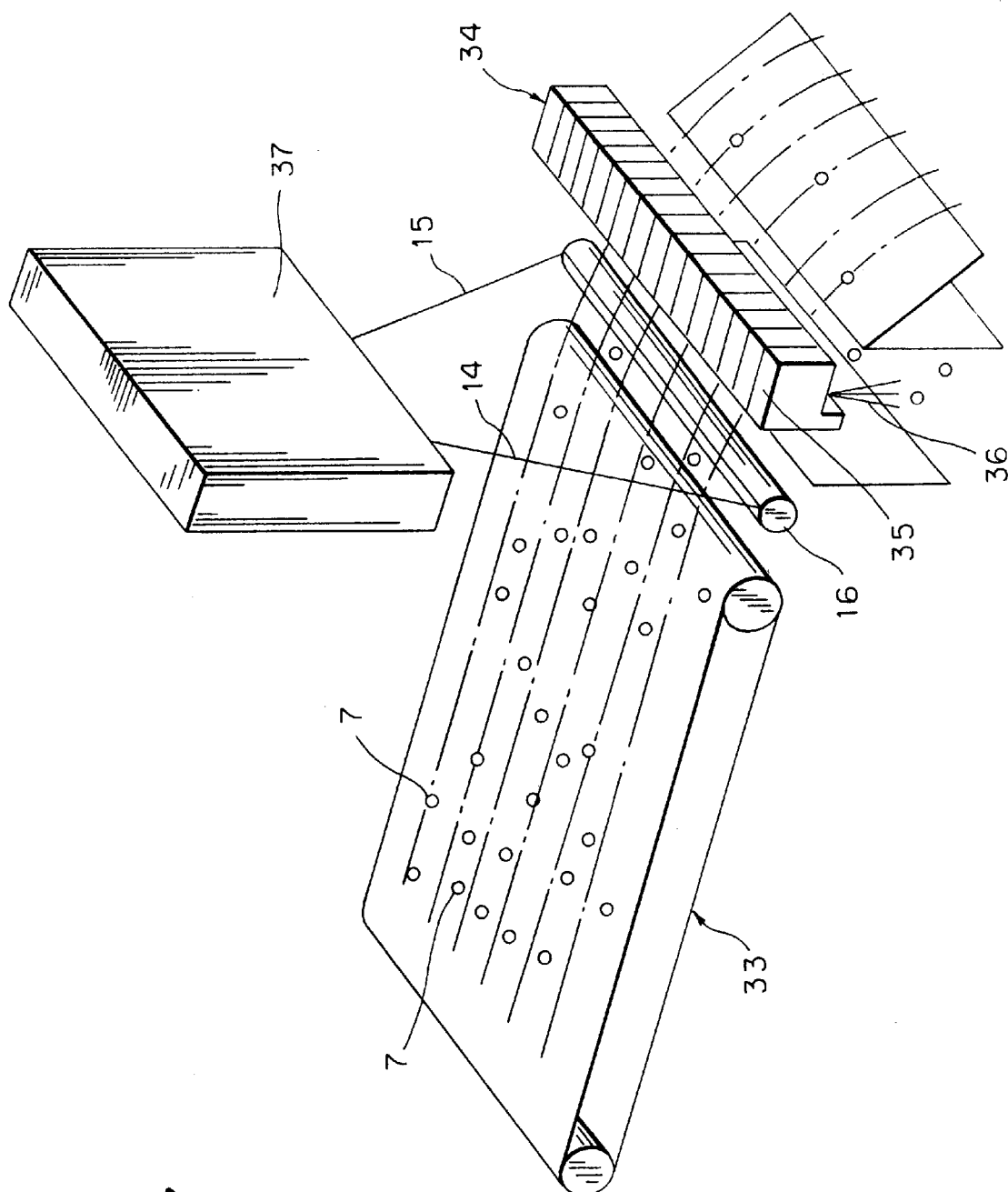
FIG. 3 is a schematic perspective representation of a sorting apparatus with a conveyor belt according to the invention.

FIG. 3 shows a traditional sorting apparatus for products consisting of parts 7 that are loose from one another, for example granular products, provided with a conveyor belt 33, a compressed air device 34 forming a removal system, and the device 37 as described above with said tube 16. With the help of the conveyor belt 33, the parts 7 are moved through the detection zone over this tube 16. The conveyor belt 33 extends to the tube 16 in such a manner that the parts 7, which are moved by the conveyor belt 33 in the direction of the detection zone and the tube 16, are travelling at a sufficiently high velocity when leaving the conveyor belt 33 to move successively through the detection zone, over the tube 16 and past the compressed air device 34.

In the detection zone, these parts 7 are recognised by the device 37 described above as being lower-value parts or foreign objects or as being good parts. When a part 7 is identified as a foreign object or a lower-value part, said compressed air device 34 is activated. In particular, a valve 35 of said compressed air device 34 is opened, where said valve is in a position corresponding to said foreign object or lower-value part. In this way a powerful, directed current of air 36 is created which removes the foreign object or lower-value part from the product.

In current sorting apparatuses, as shown in FIG. 3, the signal generated by said detector 12 or 13, represented by the curve 17 in FIG. 2, has a maximum 18 for the position where the band 2 falls on said side 5 at an angle of substantially 45°, and a considerably weaker signal 19 is obtained when the band 2 is in one of the extreme positions 14 or 15.

In general, a weaker signal is obtained whenever the length of the band 2 between the prismatic mirror 4 and the tube 16 is essentially at its smallest. Accordingly, a signal is obtained as represented by the convex curve 17, as a function of the position of the light band 2.

According to the state of the art, the signal thus generated is divided into a number of small intervals 17', where the signal of a particular interval 17' is amplified to a certain value so that a final signal is obtained that is independent of the position of the light band 2 when the latter falls on the tube 16. Modifying this signal is done by means of suitable electronics, for example by multiplying the signal for a particular interval 17' by a suitable factor.

Whenever the light band 2 is directed toward a lower-value part or a foreign object, the signals 17 generated by the detector 12 or 13 lie above or below predetermined thresholds, and said lower-value part or foreign object is then ejected from the product stream. In order to be able to compare the signal from such a lower-value part or foreign object with said thresholds and with the signal for a good part, the latter signal must also be amplified for the corresponding interval 17'.

It is preferable for the device in FIG. 1, however, to compare the value for a predetermined ratio of the signal values generated by each of the two detectors 12 and 13 with the ratio for a good part in order to determine whether a part 7 of the product shows an irregularity, and therefore whether it is a foreign object or lower-value part.

In certain cases, the signal generated by a detector 12 or 13 is compared with a reference signal that has a similar shape to the curved signal 17 as shown in FIG. 2. However, comparing a ratio or combination of the signals from different detectors 12 and 13 with particular thresholds is a highly complex operation because of the curved shape of the signal 17 for each of the detectors 12 and 13.

The above methods of compensating for the curved shape of the signal 17 do not however result in uniform sensitivity of said device when it is used for a product containing discrete parts, i.e. parts that are loose from one another. For instance, it is possible that a part which is characterised as a lower-value part or a foreign object in a position corresponding to 14 or 15 of said light band 2 may nevertheless be characterised as a good part when for example it is located in the middle of the detection zone, where the light band 2 falls essentially vertically on the tube 16.

The curved shape of the signal 17 is due to among other things the variation in the angle at which said light band falls on the tube 16, as a result of which the scattered light will have a maximum intensity in a corresponding varying direction.

In addition, the percentage reflection, which is dependent on the angle of incidence of the band 8''' of scattered light on a face 5, varies according to the position of the light band 2 and contributes to the curved shape of the aforesaid signal.

As a result of the rotation of the mirror 4, and the corresponding change in orientation of the face 5, the area of the beam splitter 9 illuminated by the scattered light 8''' is not always the same, as is shown in FIGS. 4, 5 and 6.

The solid angle of the band of scattered light 8''' falling on the face 5 also varies according to the position of said face 5, and thus of the light band 2. This solid angle falling on a face 5 is at its greatest when the distance between the point at which the band 2 falls on the mirror and the corresponding point at which it falls on the tube 16 is at its smallest.

FIGS. 4, 5 and 6 schematically show the cross section of the band of scattered light 8''' in a different position each time, represented by a shaded rectangle 30, 31, 32 and 30', 31' and 32, as observed by the aforesaid detectors.

According to a preferred embodiment of the method according to the invention, the passage of the scattered light 8''' to said detector 12 or 13 is adjusted according to the position of the light band 2, so that the latter always comes in at essentially the same solid angle. This ensures that the light stream 8''' of the light 8 scattered by part 7 and falling on the detector 12 or 13 is independent of the position of said part 7 in said detection zone, or in other words independent of the position of said light band 2. In this way, a substantially uniform sensitivity is obtained when qualifying the parts 7 of the product to be sorted.

Figure 7:
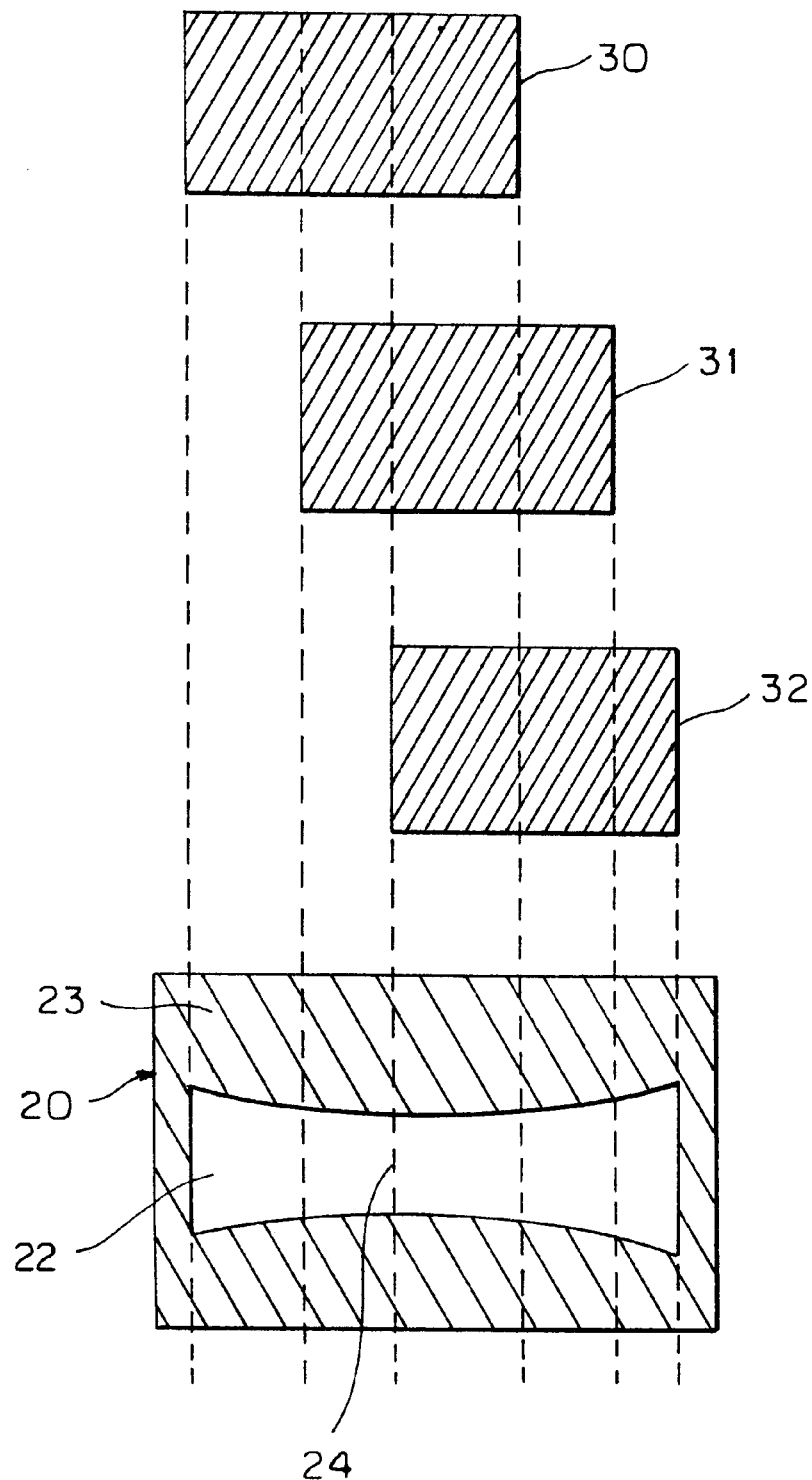
FIG. 7 is a schematic representation of an embodiment of a diaphragm according to the invention.

For this purpose, the device according to the invention is provided with an adjusting element 20, more specifically a diaphragm 23, as shown in FIG. 7. This diaphragm 23 has an opening 22 with a progressive narrowing in the direction of the point on which, globally seen, the greatest stream of scattered light 8''' falls. This narrowing 24 is arranged in a direction perpendicular to the plane in which said light band 2 moves. The form and the size of the opening 22 in the diaphragm 23 are therefore chosen so that whenever said light band 2 is directed towards the product, the signal generated by the detector 12 or 13 on which said scattered light 8''' falls is substantially independent of the position of said light band 2.

For this purpose, as shown in FIG. 7, the diaphragm can be asymmetrical, so that, for example, the split formed by said opening 22 has a different width at either end. In addition, said narrowing 24 does not necessarily have to be in the middle part of said opening 22.

In a particular embodiment of the device according to the invention, said diaphragm 23 has means to adjust the size and the shape of said opening 22 to suit the specific requirements or characteristics of the device or of the sorting apparatus.

Figure 8:
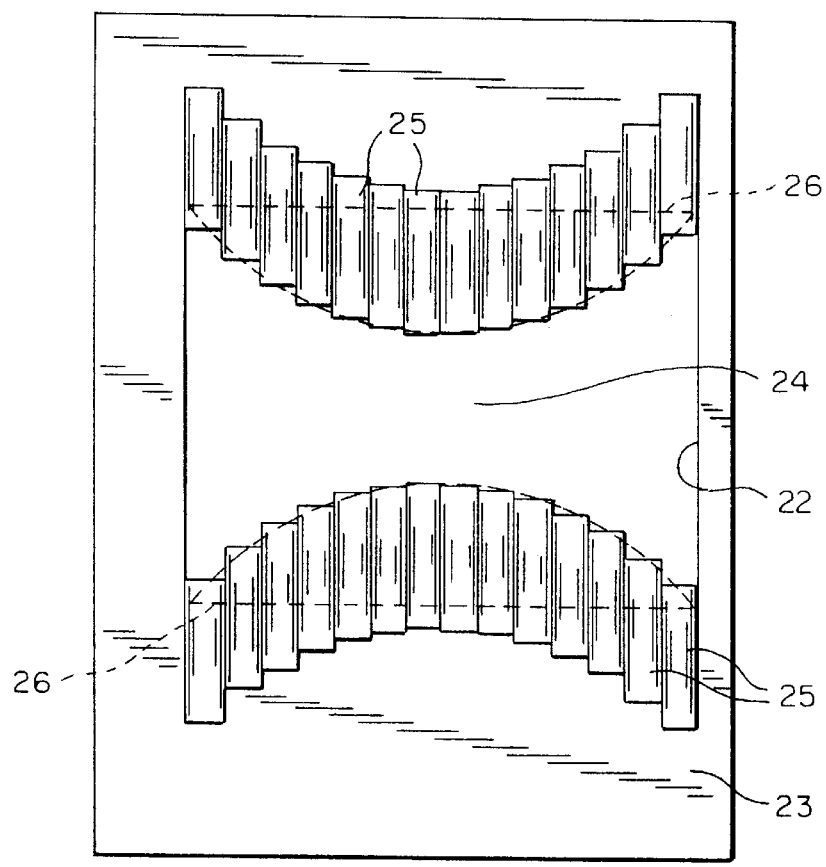
FIG. 8 is a schematic representation of a second embodiment of a diaphragm of a sorting apparatus according to a specific embodiment of the invention.

Such a diaphragm 23 is shown in FIG. 8. This diaphragm 23 is provided with a rectangular opening 26, with small, movable plates 25 on either side of said opening 26. These plates 25 are rectangular and extend in their longitudinal direction perpendicular to the edge of said opening 26. By moving said plates 25 in relation to one another and to the opening 26, the opening 22 of said diaphragm 23 can be adjusted.

Preferably, the end of the plates 25 facing said opening 22 are oblique to a certain extent, so that after the adjustment of said opening 22, the latter has an approximately continuous edge.

Figure 10:
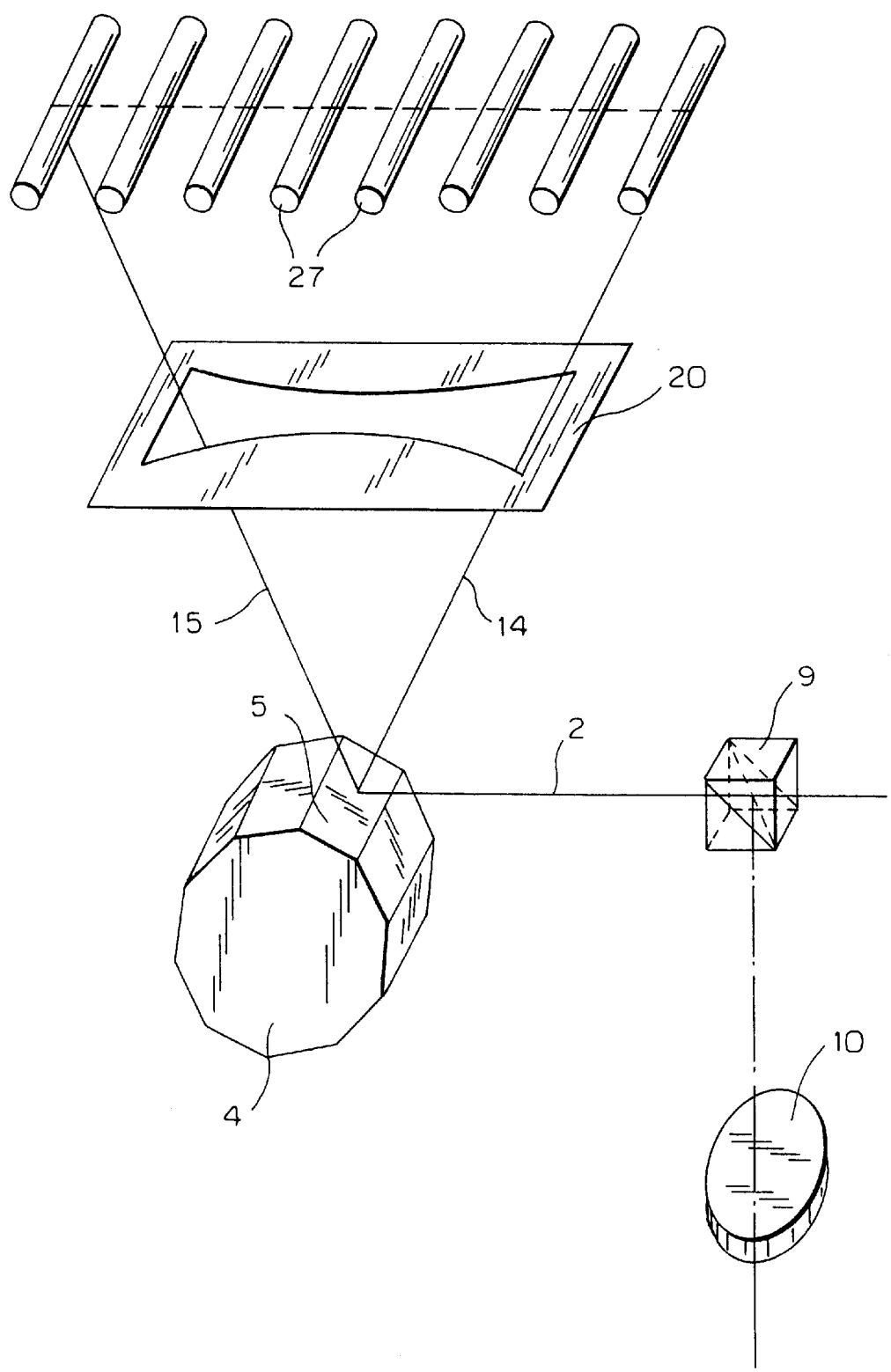
FIG. 10 is a schematic perspective representation of an important part of a detection system with simulation parts and an adjusting element.

In order to adjust the opening 22 of said diaphragm 23, simulation parts 27 are placed in the detection zone, as is shown in FIG. 10. These simulation parts 27 are formed by little bars which preferably have a cross-section that is essentially the same as that of the parts 7 of the product to be sorted. The simulation parts 27 are placed with the longitudinal axis perpendicular to the plane formed by the moving band 2. The light stream of the scattered light from these simulation parts that falls on said detector 12 or 13 is then adjusted until a constant signal 17 is obtained, by adjusting the opening 22 of the diaphragm 23 with the help of the movable plates 25.

Preferably, the opening 22 of the diaphragm 23 will first be adjusted to a position where the detector 12 or 13 has the lowest value.

Figure 9:
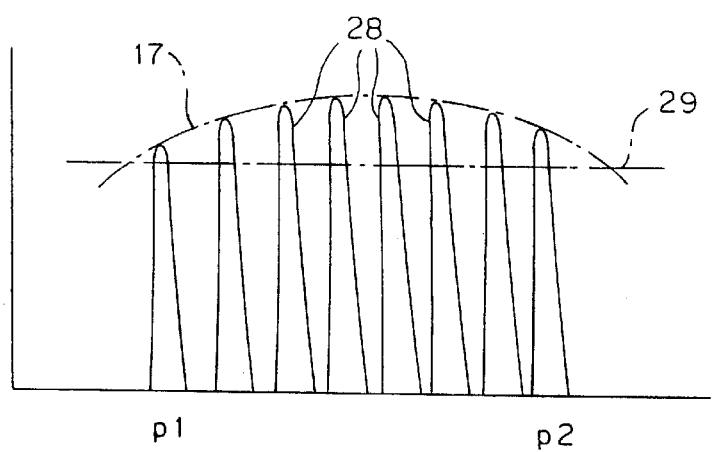
FIG. 9 is a graph of the signal supplied by a detector when a light band falls on simulation parts.

FIG. 9 shows a graph of the signal generated by the detector 12 or 13 when the light band 2 is moved across said simulation parts 27 and when said tube 16 scatters essentially no light from the light band 2. This graph shows the different peaks 28 corresponding to the signal generated by the detector 12 or 13 for the corresponding simulation parts 27. By adjusting the opening 22 with the help of the plates 25, these peaks 28 are reduced to a constant value, as shown by line 29. In this way, the diaphragm 23 will show an opening 22 with a shape as shown schematically in FIG. 10.

In a simplified method for adjusting the diaphragm 23, an object that scatters said light band 2, such as a part 7 of the product, is brought into various positions in said detection zone or moved through said detection zone, with the opening 22 of the diaphragm 23 being adjusted so that the signal generated by the detector 12 and 13 has the same value for every position of that object.

In the sorting apparatus according to the invention, said adjusting element 20, more specifically a diaphragm 23, can be mounted between said detection zone and the polygonal mirror 4, as shown in FIG. 10.

Figure 11:
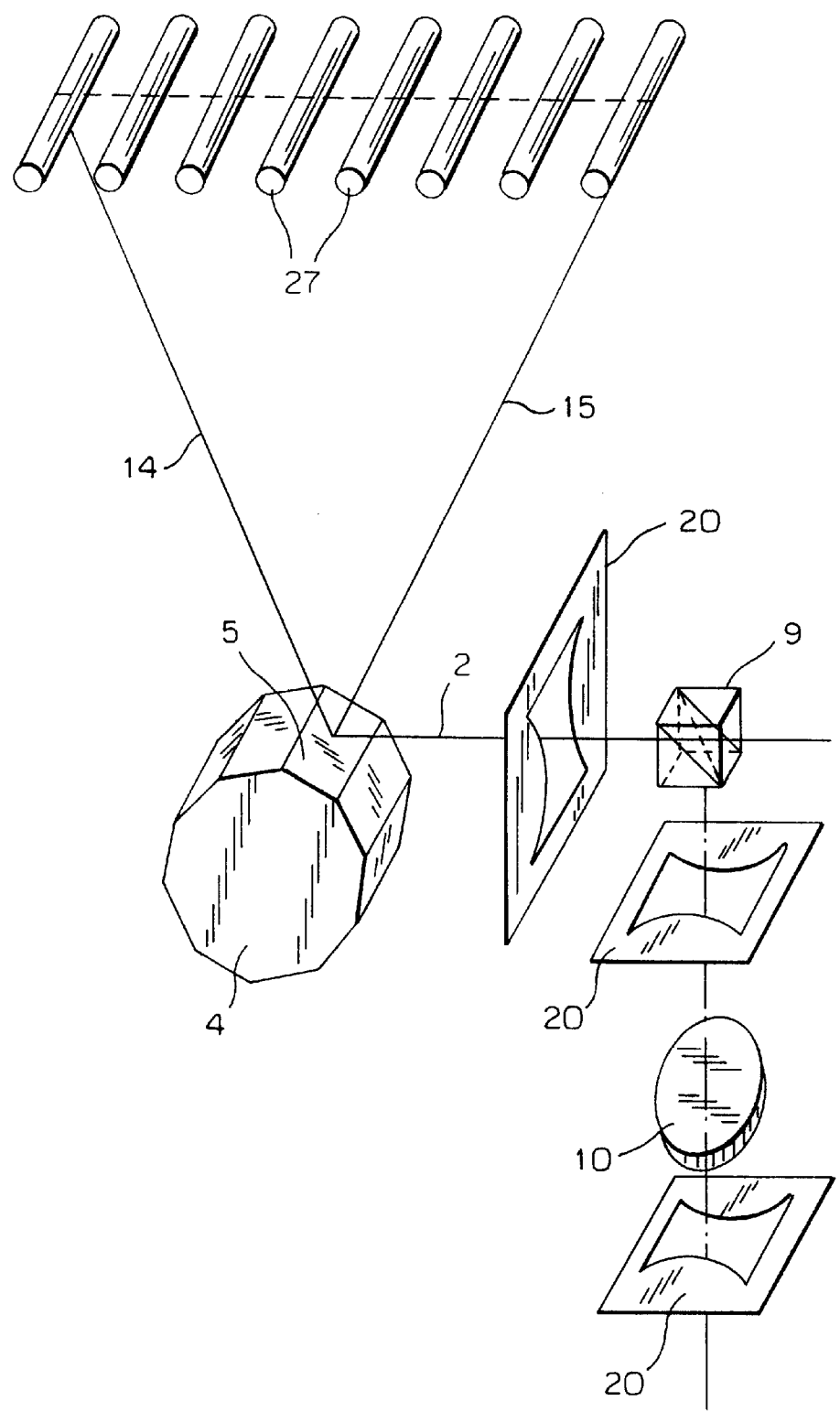
FIG. 11 is a schematic perspective representation of an important part of a detection system with an adjusting element shown in different positions.

FIG. 11 shows some other possible positions for this adjusting element 20, namely between the mirror 4 and the beam splitter 9, or between said beam splitter 9 and a lens system 10, or in front of the detector 13. This adjusting element 20 can in principle be positioned at all places where the light stream 8''' falling on the detector 12 or 13 moves in accordance with the position of the light band 2.

The invention is of course not limited to the embodiments of the method and the sorting apparatus according to the invention as described above and shown in the accompanying drawings. For example, the adjusting element 20 can consist of a light filter which progressively lets more light through to the detector 12 or 13, depending on the proximity of the light band 2 to the positions 14 or 15. Sometimes it is possible to adjust the sensitivity of the detector 12 or 13 so that the device according to the invention forms part of said detector. Another possibility is to give the faces 5 of the prismatic mirror 4 such a shape or reflection characteristics that said adjusting element 20 coincides with each of said faces 5 by, for example, covering part of those faces 5. In that case, however, a diaphragm will have to be mounted between the moving mirror 4 and said detectors 12 and/or 13, in such a manner than said diaphragm lets through only part of the scattered light reflected by a face 5 to said detectors. By partially covering the face 5 in combination with the latter diaphragm, the light stream falling on said detector 12 and/or 13 is influenced according to the position of the face 5, and thus according to the position of the light band 2.

It is also possible for the rotating mirror 4 to be replaced by another moving mirror, such as a rapidly vibrating mirror.

The sorting apparatus can, if required, also work with several light bands, said light bands being preferably laser beams or bands. The number of detectors need not necessarily be related to the number of light bands. For example, one frequency of scattered light may be detected by several detectors.

By "light" in this description is meant all electromagnetic radiation, preferably with a wavelength of between 100 nm and 10,000 nm. In most cases, however, light with a wavelength of between 400 and 1,200 nm will be used.

In some cases, the aforesaid device has no tube 16. Apart from being used in sorting apparatuses for sorting e.g. French fries, peas, raisins and other granular products, the device according to the invention can be used for monitoring the quality of and/or irregularities in a product or parts of a product. Thus, for example, the product can consist of a continuous material such as a steel plate, a plastic film, a strip of paper or a woven textile, with the device being moved relative to the surface of the product in order to detect irregularities in it.

What is claimed is:

1. Method for detecting irregularities in a product, in which at least one light band (2), consisting of at least one laser beam or a light beam, is directed towards said product (7), which moves in a particular direction through a detection zone, in such a manner that said band (2), which moves transversely across the direction of movement of the product (7), is at least partially scattered and/or reflected by said product (7), where the scattered light is separated from the reflected light and captured at least partially by at least one detector (12, 13) in order to detect irregularities in the product, wherein the quantity of light scattered by a part of the product and captured by said detector (12, 13) is adjusted as a function of the position of said light band (2) by means of an adjusting element having an opening with a progressive narrowing in the direction of the point on which the greatest stream of scattered light (8''') falls so that the quantity of light captured by said detector is independent of the position of said part in said detection zone and thus independent of the position of said light band (2).

2. Device for detecting irregularities in a product that moves in a particular direction through a detection zone, with at least one detector (12, 13) and means to generate at least one light band (2) directed towards said product (7), in such a manner that the light from said light band (2) is scattered and/or reflected by part of the product (7), where the light (8) scattered by the product (7) is separated from the reflected light and at least partially captured by said detector (12, 13), wherein, between said detector (12, 13) and the detection zone through which said product (7) has to move, said device further comprises an adjusting element (20) comprising a diaphragm (23) with an opening with a progressive narrowing in the direction of the point on which the greatest stream of scattered light (8''') falls, wherein the diaphragm lets through only some of the light (8) scattered by a particular part of the product (7), in such a manner that the quantity of scattered light falling on said detector (12,13) is independent of the position of said part (7) in the detection zone.

3. Device according to claim 2, characterised in that said adjusting element (20) has a diaphragm (23) which has at least one calibrated opening (22).

4. Device according to claim 3, characterised in that said diaphragm (23) has means (25) for adjusting the size of said opening (22).

5. Device according to claim 3, characterised in that said diaphragm (20) has small, movable plates (25) at the edge of said opening (22, 26), permitting the size and/or shape of the opening (22) to be adjusted so that the light stream (8''') falling on said detector (12, 13) is independent of the position of said light band (2).

6. Device according to claim 3, characterised in that said opening (22) has a narrowing (24) in a direction perpendicular to the plane to which said light band (2) moves parallel.

7. Device according to claim 2, characterised in that said adjusting device (20) is mounted at a place where the light (8) scattered by said parts (7), and which is at least partly detected by said detector (12, 13), forms a light stream (8''') which varies according to the position of said light band (2).

8. Device according to claim 2, characterised in that said adjusting element (20) is mounted between said detection zone and a movable mirror (4), where at least some of the light (8) scattered by said parts (7) passes through the adjusting device (20) and is reflected via said mirror (4) to a beam splitter (9) which makes the scattered light (8''') fall at last partly on said detector (12, 13), and separates it from said light band (2) and from any light band reflected from said products (7).

9. Device according to claim 8, characterised in that the adjusting element (20) is mounted between said movable mirror (4) and said beam splitter (9).

10. Device according to claim 7, characterised in that said movable mirror (4) is prism-shaped and is provided with means that enable it to rotate about its central axis (6), where the faces (5) of said mirror (4) are reflective and are preferably set at the same angle to one another.

11. Device according to claim 10, characterised in that said adjusting element (20) is mounted between said beam splitter (11) and said detector (12, 13).

12. Sorting apparatus for detecting and/or separating foreign objects or lower-value parts from good parts in a product consisting of parts that are loose from one another, characterised in that it is provided with the device according to claim 2.

13. Device according to claim 2, wherein said means to generate at least one light band cause the light band to move transversely across the direction of travel of the product.

* * * * *